United States Patent
Roggenbuck (12)

(10) Patent No.: US 6,491,695 B1
(45) Date of Patent: Dec. 10, 2002

(54) APPARATUS AND METHOD FOR ALIGNING VERTEBRAE

(76) Inventor: Carl Roggenbuck, 8271 Ramsey Rd., Port Hope, MI (US) 48468

( * ) Notice: Subject to any disclaimer, the term of this patent is extended or adjusted under 35 U.S.C. 154(b) by 0 days.

(21) Appl. No.: 09/434,129

(22) Filed: Nov. 5, 1999

(51) Int. Cl.⁷ .................. A61B 17/68; A61B 17/70; A61B 17/88
(52) U.S. Cl. .................. 606/61; 606/60; 606/105
(58) Field of Search .................. 606/60, 61, 57, 606/58, 90, 99, 105

(56) References Cited

U.S. PATENT DOCUMENTS

| | | | | |
|---|---|---|---|---|
| 3,486,505 A | * | 12/1969 | Morrison | 606/61 |
| 4,714,469 A | | 12/1987 | Kenna | 623/17 |
| 4,863,476 A | | 9/1989 | Shepperd | 623/17 |
| 4,961,740 A | | 10/1990 | Ray et al. | 606/61 |
| 5,015,247 A | | 5/1991 | Michelson | 606/61 |
| 5,431,658 A | | 7/1995 | Moskovich | 606/99 |
| 5,439,463 A | * | 8/1995 | Lin | 606/61 |
| 5,443,514 A | | 8/1995 | Steffe | 623/17 |
| 5,454,365 A | | 10/1995 | Bonutti | 600/204 |
| 5,601,556 A | | 2/1997 | Pisharodi | 606/61 |
| 5,665,122 A | | 9/1997 | Kambin | 623/17 |
| 5,697,977 A | | 12/1997 | Pisharodi | 623/17 |
| 5,865,848 A | | 2/1999 | Baker | 623/17 |
| 5,893,890 A | | 4/1999 | Pisharodi | 623/17 |
| 5,906,616 A | | 5/1999 | Pavlov et al. | 606/61 |
| 5,910,143 A | | 6/1999 | Cripe et al. | 606/87 |
| 5,947,971 A | | 9/1999 | Kuslich et al. | 606/80 |
| 6,010,502 A | * | 1/2000 | Bagby | 606/61 |
| 6,063,088 A | * | 5/2000 | Winslow | 606/61 |
| 6,120,503 A | * | 9/2000 | Michelson | 606/61 |
| 6,126,660 A | * | 10/2000 | Dietz | 606/61 |
| 6,136,001 A | * | 10/2000 | Michelson | 606/61 |
| RE37,005 E | * | 12/2000 | Michelson et al. | 606/99 |
| 6,197,033 B1 | * | 3/2001 | Haid, Jr. et al. | 606/99 |
| 6,217,579 B1 | * | 4/2001 | Koros | 606/61 |

FOREIGN PATENT DOCUMENTS

DE 19750382.9 11/1997

OTHER PUBLICATIONS

Surgical Dynamics/PLIF Surgical Technique Manual 2.0 Ray Threaded Fusion Cage.

* cited by examiner

Primary Examiner—Kevin Shaver
Assistant Examiner—Michael B. Priddy
(74) Attorney, Agent, or Firm—John J. Swartz

(57) ABSTRACT

Apparatus for aligning misaligned vertebrae including a partible screw which can be threadedly coupled to misaligned vertebrae and decoupled from the vertebrae after being aligned. The screw, which is rotatable about an axis, includes axially shiftable screw halves having complementally formed partial screw thread sections which can be aligned in any one of a plurality of axially spaced apart positions to define a helical screw thread. Apparatus is provided for detachably holding the screw halves together in any one of a plurality of axially spaced apart positions with the partial screw threads on each of the halves in alignment including an alignment collar and a locking collar which can be detachably threadedly received on, and locked to, the screw thread sections in locking positions when the screw is being threadedly coupled to and uncoupled from the vertebrae. The alignment collar and locking collar can be individually unthreaded and moved to a remote position removed from the screw threads to allow the screw halves to be axially relatively shifted relative to each other.

73 Claims, 9 Drawing Sheets

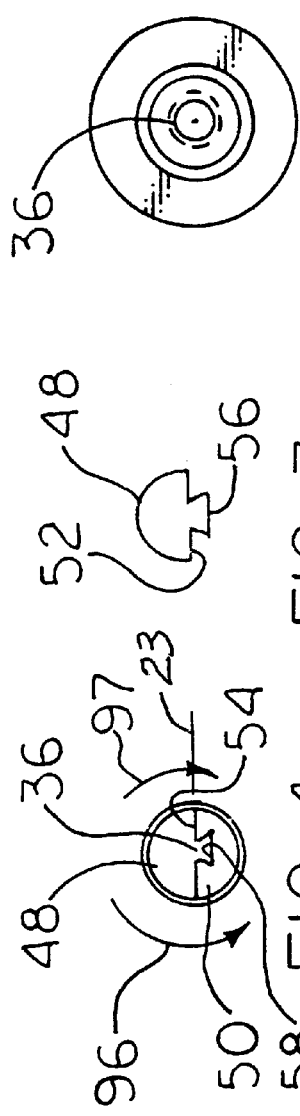
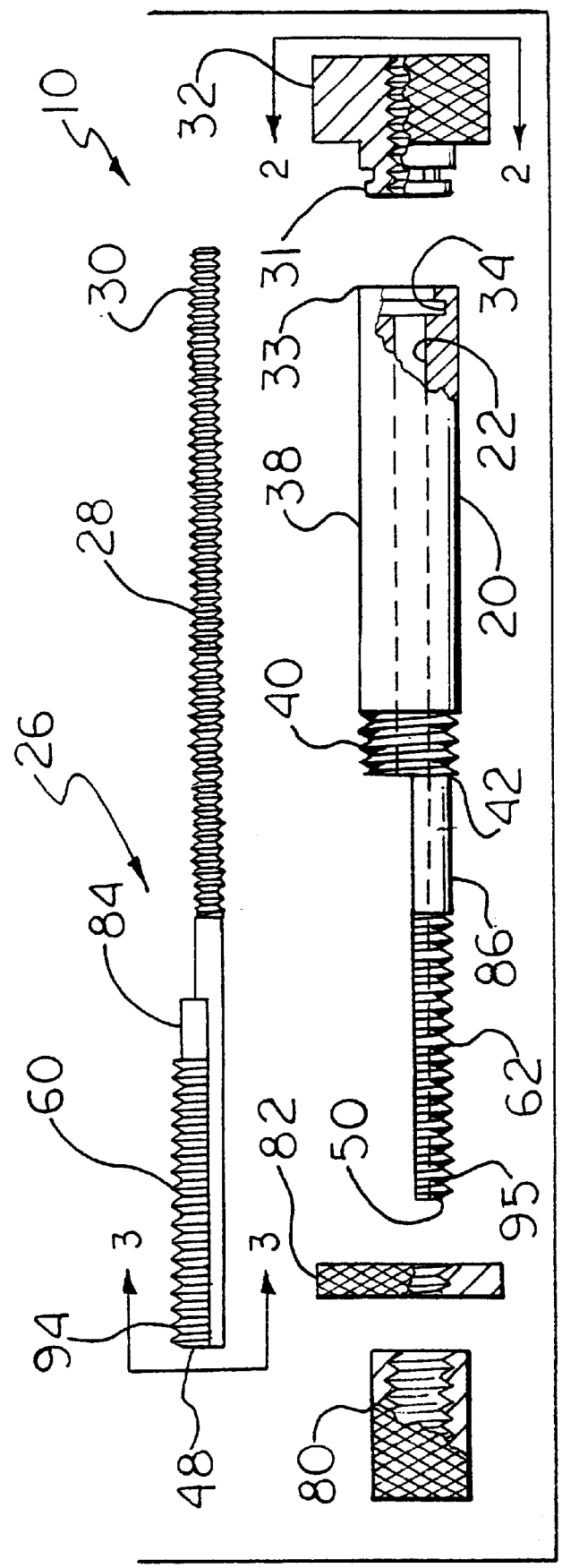
FIG. 2
FIG. 3
FIG. 4
FIG. 1

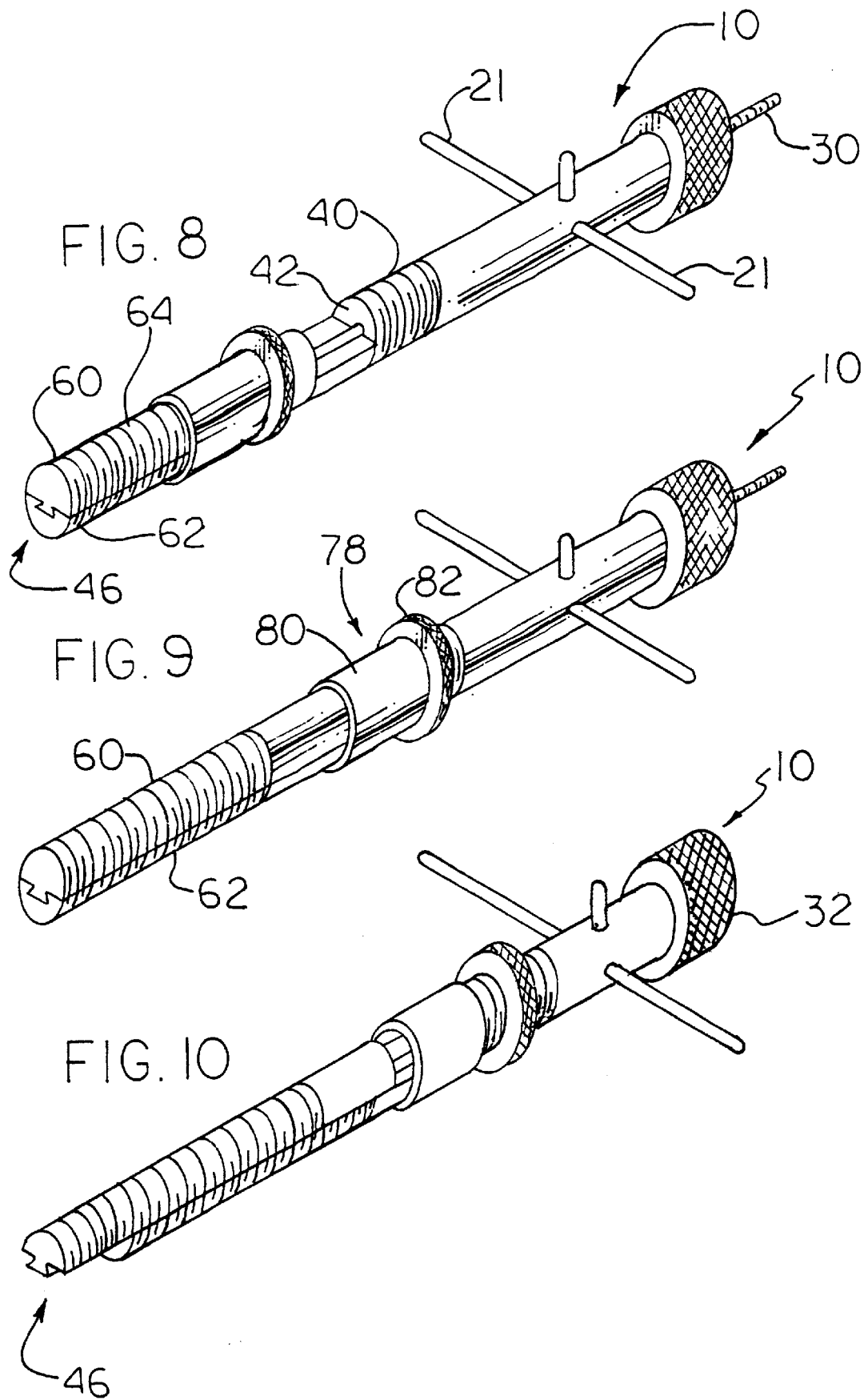

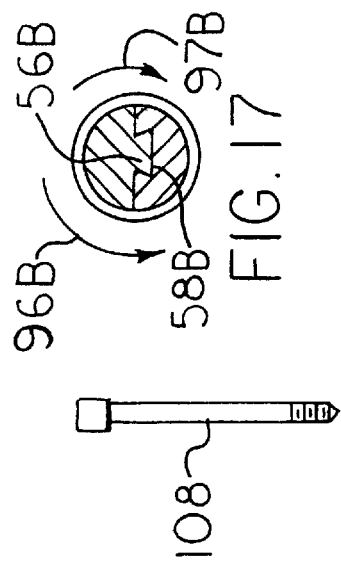
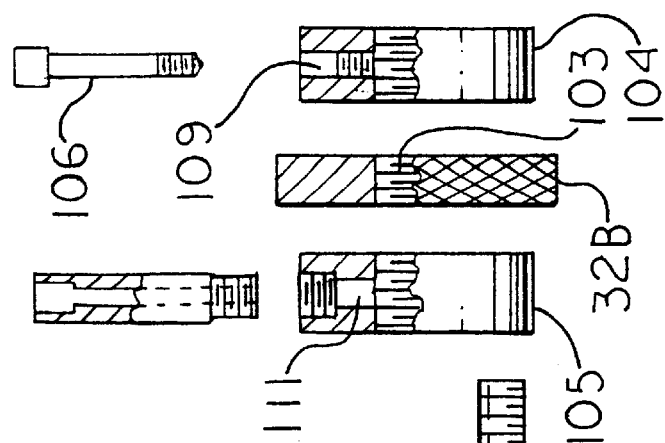
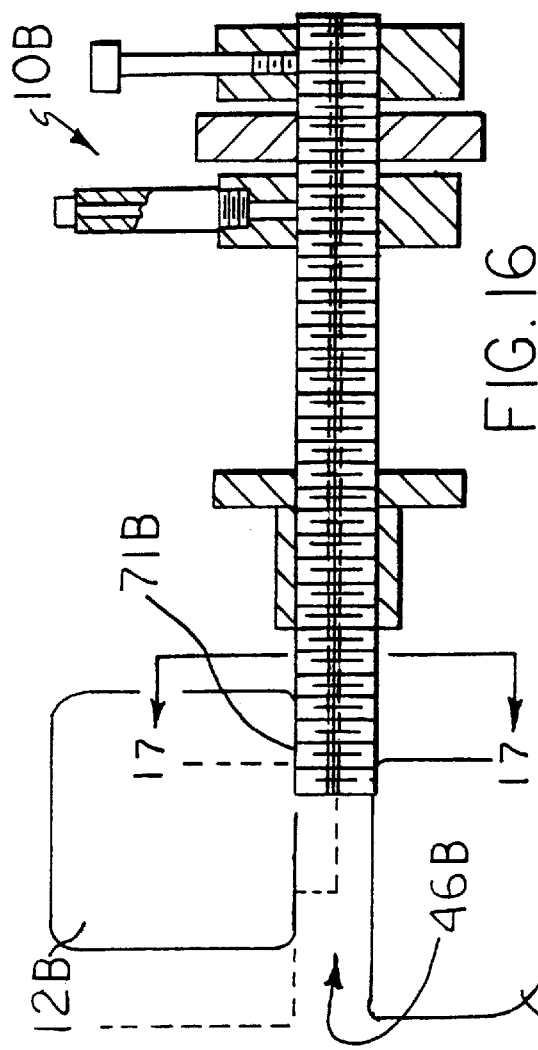
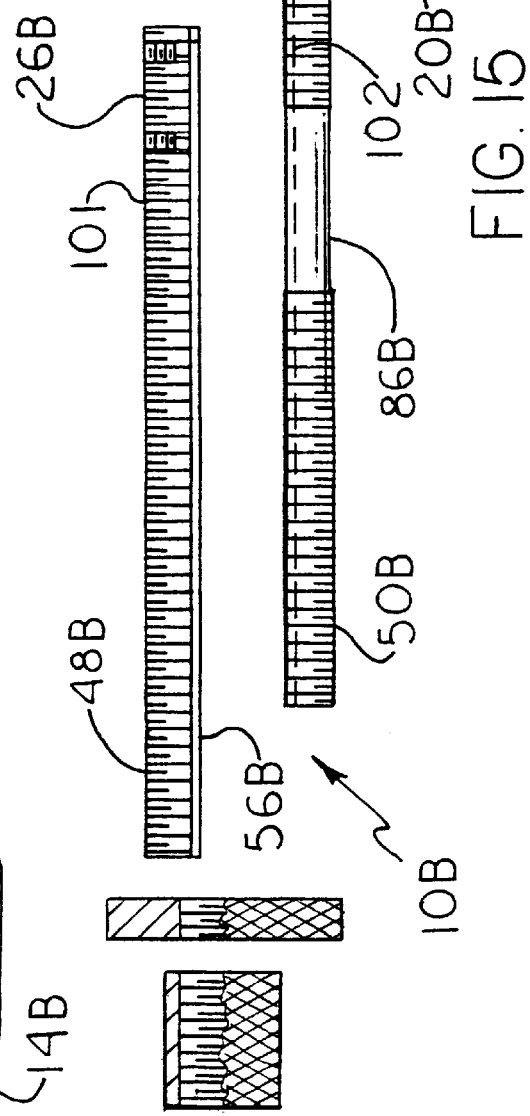

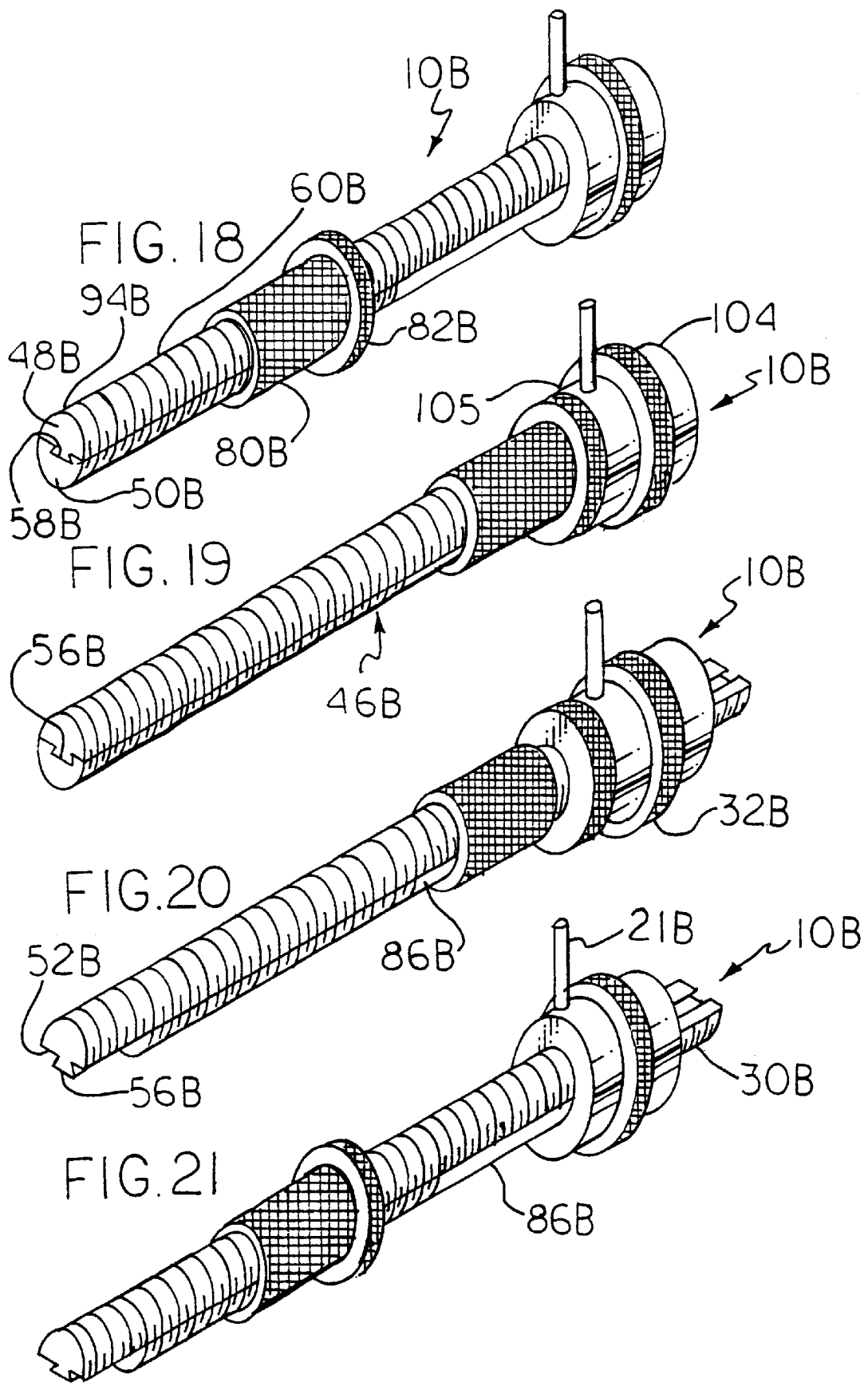

APPARATUS AND METHOD FOR ALIGNING VERTEBRAE

BACKGROUND OF THE INVENTION

1. Field of the Invention

This invention relates to apparatus and method for aligning misaligned adjacent vertebrae and more particularly to a new and improved partible vertebrae alignment screw with axially shiftable thread sections that will threadedly couple to a tapped thread cut into the misaligned vertebrae, relatively slide to relatively shift the vertebrae, and threadedly decouple from the aligned vertebrae while maintaining the integrity of the tapped thread.

2. Description of the Prior Art and Objects

Spinal injuries, diseases and other degenerative disorders of the spine have caused substantial problems and pain to a substantial number of patients. Various devices have been provided heretofore for preventing progressive degeneration and instability of the spine. One such technique has involved bone fusions which fuse adjacent spinal vertebrae to each other to prevent relative movement therebetween. Such fusions frequently follow the removal of all or a portion of a disc normally found between the adjacent vertebrae.

To aid in the fusion process, hollow threaded cages, packed with bone chips or other bone growth inducing substances, have been disposed in the intervertebral space between the adjacent vertebrae and threadedly coupled to confronting portions of the adjacent vertebrae. Such fusion cages are illustrated in U.S. Pat. No. 4,961,740 issued to Charles D. Ray, et al, on Oct. 9, 1990; U.S. Pat. No. 5,015,247 issued to Gary K. Michaelson on May 14, 1991; U.S. Pat. No. 5,906,616 issued to Paul W. Pavlov, et al on May 25, 1999; and U.S. Pat. No. 5,947,971 issued to Steven D. Kuslich on Sep. 7, 1999.

Prior to threadedly coupling the fusion cage to the vertebrae, confronting portions of adjacent misaligned vertebrae are drilled and tapped to provide a thread for receiving the thread of the fusion cage as more particularly illustrated in the PLIF Surgical Technique Manual 2.0, Ray Threaded Fusion Cage™, published by Surgical Dynamics Inc, 111 Glover Avenue, Norwalk, Conn., which is incorporated hereby by reference as though fully set forth herein. The vertebrae to be fused together should be properly aligned prior to the fusion. When the adjacent vertebrae are out of alignment with each other, which is a condition sometimes referred to as spondylolisthesis, they are to be moved back into alignment prior to the insertion of the fusion cage. Toward this end, apparatus, such as that disclosed in the German Patent Publication No. 197 50 382.9 dated Nov. 13, 1997, has been utilized to realign the vertebrae.

The German Patent Publication No. 19750382.9 discloses a screw which can be threaded into a thread previously tapped into confronting portions of misaligned vertebrae. Portions of the screw in the aforementioned German patent publication are anchored to adjacent vertebrae and axially shifted relative to each other to shift the vertebrae into alignment. The screw is then unturned and a hollow threaded cage is turned into the threaded space vacated by the screw. With the aforementioned prior art German construction, it is difficult to insure that the partial screw threads on each of the partible halves are in helical alignment with the partial screw threads on the other partible half so that the helical thread tapped into the adjacent vertebrae is not damaged by the partial screw threads on the partible halves being out of helical alignment with each other and not following the same helical path. Accordingly, it is an object of the present invention is to provide a new and novel method and apparatus for repositioning misaligned vertebrae.

It is another object of the present invention to provide new and novel vertebrae aligning apparatus which is threadedly received by a tapped thread provided on confronting portions of adjacent misaligned vertebrae and which can be removed, without damaging the tapped thread after portions of the screw have been shifted to align the vertebrae.

Apparatus for shifting vertebrae for the reduction of spondylolisthesis is illustrated in U.S. Pat. No. 5,601,556 issued to Madhavan Pisharodi on Feb. 1, 1997, including an insert that is disposed between adjacent vertebrae and then rotated 90° before and after shifting of the vertebrae. The Pisharodi device is not threaded into and out of the vertebrae and is not concerned with preserving the integrity of a tapped screw thread which threadedly receives a fusion cage.

Another object of the present invention is to provide a new and novel vertebrae alignment tool which will align misaligned vertebrae including axially partible screw thread sections having complementally formed partial screw threads thereon that can be moved to any selected one of a plurality of axially spaced apart positions in which the partial screw threads on one screw thread section are helically aligned with the partial screw threads on the other screw thread section.

Still another object of the present invention is to provide a vertebrae alignment tool of the type described which includes a new and novel locking device for locking the partible screw thread sections together when they are being threaded into and out of the adjacent vertebrae.

Yet another object of the present invention is to provide apparatus for aligning misaligned vertebrae of the type described including an alignment nut which is threadedly received by axially partible screw sections in any selected one of a plurality of axially spaced apart positions to insure that the partial screw threads on one-half of the screw are held in helical alignment with the partial screw threads on the other half of the screw as the screw is being threadedly coupled to misaligned vertebrae and threadedly decoupled from aligned vertebrae.

Still yet another object of the present invention is to provide a new and novel vertebrae repositioning tool of the type described which includes an alignment nut that is threadedly received on axially partible screw halves having first and second pluralities of partial screw threads that are helically aligned to form a helical thread on a screw that is threadedly coupled to adjacent misaligned vertebrae and a locking nut for locking the alignment nut to the screw halves to prevent relative movement therebetween as the screw is being threadedly coupled to misaligned vertebrae and decoupled from aligned vertebrae.

A further object of the present invention is to provide alignment apparatus for aligning misaligned vertebrae including new and novel elongate bodies for mounting partible screw halves which are axially slidably coupled to each other.

A still further object of the present invention is to provide alignment apparatus of the type described including new and novel mechanism for axially shifting the elongate bodies relative to each other to axially shift the screw head.

Another object of the present invention is to provide a new and novel method of aligning first and second vertebrae including axially locking a pair of screw halves together as the screw halves are being threadedly coupled to and decoupled from adjacent vertebrae and for unlocking the screw halves and axially shifting the screw halves between the coupling and decoupling steps.

It is another object of the present invention to provide apparatus for shifting and aligning adjacent vertebrae in preparation for, and during the process of, securing the vertebrae with a fusion cage screw sometimes sold under the trademark "Ray Threaded Fusion Cage™".

Another object of the present invention is to provide new and improved vertebrae alignment method and apparatus which will prepare more qualified candidates for the cage screw method of fusing vertebrae than that which existed in the prior art.

A still further object of the present invention is to provide a method of aligning misaligned adjacent vertebrae including the steps of: threadedly coupling an axially partible vertebrae displacing head, having first and second abutting screw halves, provided with half screws, which are helically aligned to form a helical screw thread, coupled to adjacent misaligned vertebrae; axially relatively shifting the screw halves opposite directions to shift the misaligned vertebrae into alignment, detachably locking the screw halves together in the axially displaced positions with the half threads in helical alignment to preclude axial movement therebetween, and axially unthreading the vertebrae displacing head from the vertebrae with the abutting screw halves held together to prevent relative axial shifting therebetween.

Other objects and advantages of the present invention will become apparent to those of ordinary skill in the art as the description thereof proceeds.

SUMMARY OF THE INVENTION

Apparatus for repositioning misaligned vertebrae comprising an alignment head, having first and second axially partible screw halves forming first and second screw thread sections which cooperate in a plurality of axially spaced positions to form a helical screw on the head, which is rotatable about a longitudinal axis in a first direction between the vertebrae to a position in which the first and second screw thread sections each threadedly engage only one of the vertebrae and oppositely rotatable to an unthreaded position removed from the vertebrae after the vertebrae are repositioned; mechanism for relatively axially shifting the first and second axially partible screw halves, while threadedly coupled to separate ones of the adjacent vertebrae, in opposite directions to relatively properly reposition the vertebrae relative to each other, and mechanism for axially detachably holding the first and second screw halves together, with at least a portion of the first screw thread section in helical alignment with a portion of the second screw thread section, to preclude relative axial shifting of the first and second screw thread sections when the head is rotated in the opposite direction and threadedly decoupled from the aligned vertebrae. A method of aligning vertebrae without damaging a tapped threaded provided in adjacent misaligned teeth is also contemplated.

DESCRIPTION OF THE DRAWINGS

The invention may be more readily understood by referring to the accompanying drawings, in which:

FIG. 1 is an exploded side elevational view of a vertebrae alignment tool constructed according to the present invention, parts being broken away in section for purposes of clarity;

FIG. 2 is an end elevational view of an alignment knob nut only, taken along the line 2—2 of FIG. 1;

FIG. 3 is an opposite end elevational view of only one of a pair of screw halves which is to be threadedly coupled with one of the misaligned vertebrae, taken along the line 3—3 of FIG. 1;

FIG. 4 is a sectional end view, taken along the section line 4—4 of FIG. 5, more particularly illustrating both of the screw halves in assembled relation and a dove tail coupling between the screw halves;

FIG. 8 is a perspective view of the alignment tool illustrated in FIGS. 1–7, illustrating the screw halves in coextensive abutting positions threadedly receiving an alignment nut and a locking nut when the tool is to be threadedly coupled to the misaligned vertebrae in the positions illustrated in FIG. 6;

FIG. 9 is a similar perspective view of the alignment tool illustrated in FIGS. 1–8 but illustrating the alignment nut and locking nut in unthreaded remote dwell positions allowing the screw halves to be axially displaced relative to each other after they have been threadedly coupled to adjacent misaligned vertebrae in the positions illustrated in FIG. 6;

FIG. 10 is a similar perspective view of the alignment tool illustrating the screw halves in adjusted axially displaced positions, such as that illustrated in chain lines in FIGS. 5 and 7, after the adjacent vertebrae have been aligned;

FIG. 15 is an exploded view of a second modified embodiment of a vertebrae repositioning tool constructed according to the present invention, parts of the tool being broken away in section for purposes of clarity;

FIG. 16 is a sectional side view of the alignment tool illustrated in FIG. 15 with the adjacent screw halves threadedly coupled to a pair of misaligned adjacent vertebrae, the screw halves and vertebrae being illustrated in chain lines in adjusted positions in which the adjacent vertebrae have been moved into alignment;

FIG. 17 is a sectional end view, taken along the section line 17—17 of FIG. 16 more particularly illustrating the dove tail coupling between the abutting screw halves;

FIG. 18 is a perspective view of the alignment tool with the parts positioned as illustrated in FIG. 16;

FIG. 19 is a similar perspective view illustrating the alignment nut and locking nut in non-threaded dwell positions allowing the screw halves to be relatively shifted;

FIG. 20 is a similar perspective view illustrating the position of the alignment tool in a subsequent step in the operation wherein the screw halves are relatively axially shifted to move the vertebrae from the position illustrated in solid lines to the shifted positions illustrated in chain lines in FIG. 16;

FIG. 21 is a similar perspective view illustrating the parts in the axially shifted positions, illustrated in chain lines in FIG. 16, whereby a subsequent step of decoupling can be accomplished with the screw halves axially locked together.

DESCRIPTION OF PREFERRED EMBODIMENT

Figure 5:
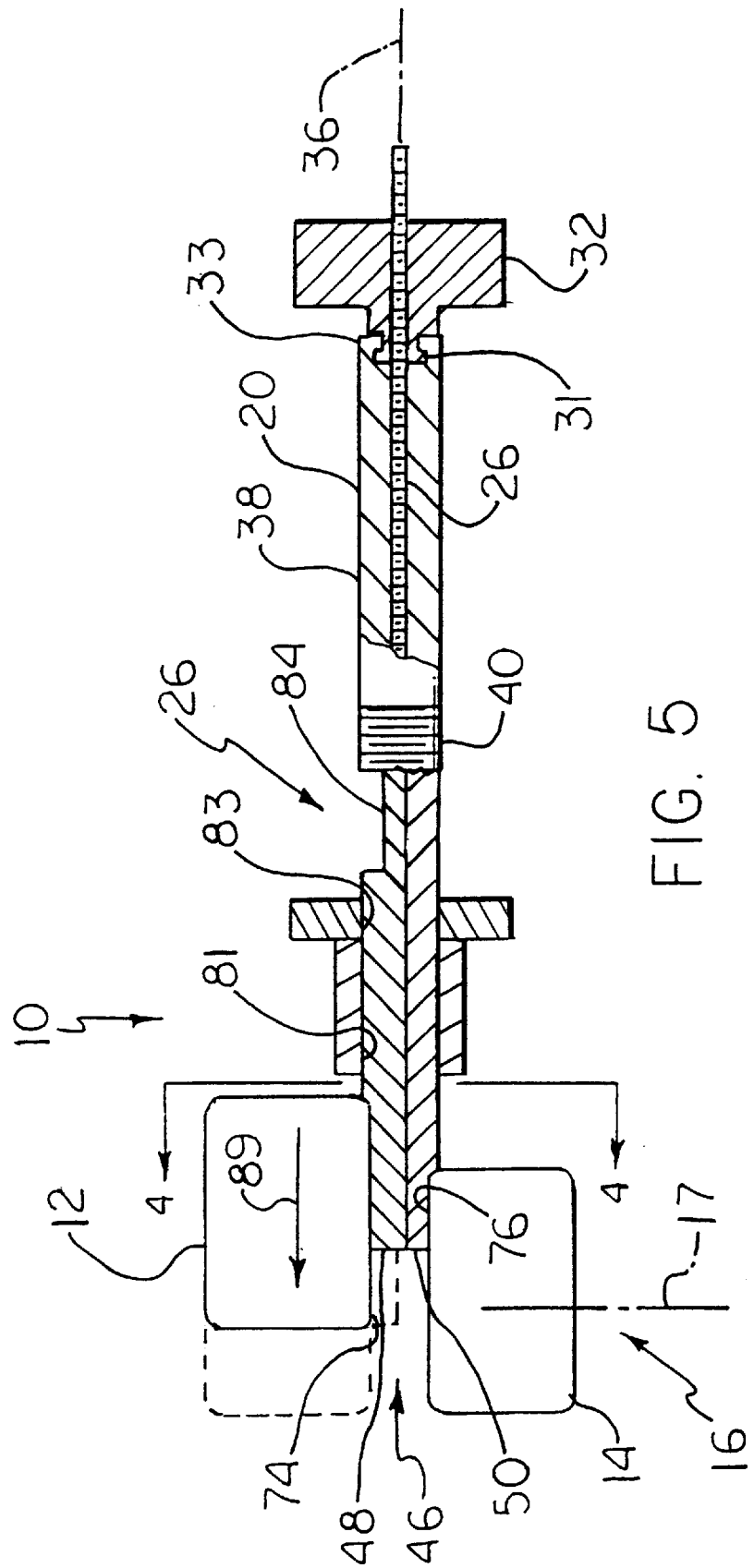
FIG. 5 is a sectional side elevational view illustrating the parts of the alignment tool constructed according to the present invention in assembled relation with the screw halves being threadedly coupled to adjacent misaligned vertebrae, the screw halves and vertebrae being illustrated in adjusted positions in chain lines in which the vertebrae are aligned.

A vertebrae alignment tool, generally designated 10, constructed according to the present invention, is particularly adapted for aligning misaligned vertebrae 12 and 14 of a spinal column, generally designated 16. An intervertebral cartilagenous disc, schematically designated 13 (FIGS. 11 and 12) which is normally disposed between the vertebrae 12 and 14, is typically removed before the tool 10 is utilized to align the misaligned vertebrae. The tool 10 includes a first elongate hollow main tool body, generally designated 20, having an elongate bore 22 therethrough for receiving a second elongate threaded body 26, generally designated. The tool body 20 has hand graspable, oppositely projecting handles 21 (FIG. 8).

The threaded body 26 includes a helical rib 28 thereon having an axially outer end 30 which is threadedly received by a slide driver knob nut 32 that has an axially inner integral keeper collar 31 rotatably journaled in a complementally formed annular slot 34 provided on an axially outer end 33 of the hollow tool body 20. As the knob nut 32 is turned, the threaded shaft 26 threadedly received therein will axially translate along its longitudinal tool axis 36. As illustrated, the bore 22 is tapered radially outwardly in an axially inward direction away from the axially outer end 33.

The outer surface 38 of tool body 20 is a smooth right circular cylindrical surface with the exception of an axially inner threaded portion 40 which comprises a threaded storage member as will be described more particularly hereinafter.

Mounted on the tool bodies 20 and 26 is an alignment screw, generally designated 46, having first and second vertebrae shifting screw halves 48 and 50, respectively, fixed to the axially inner ends 42 and 44 of the tool bodies 20 and 26, respectively. The screw half 50 is disposed on the end of tool body 26 radially outward of the bore 22 so as to allow the screw thread 28 to freely axially translate relative to the screw half 50.

As illustrated in FIGS. 3 and 4, the screw 46 is split on an axial plane 23 dividing the screw halves 48 and 50 which are semi-cylindrically shaped and include flat abutting faces 52 and 54, respectively, that lie in the plane 23 and are in mating, sliding relation and coupled together with a complementally formed dove tail slide 56 and a dove tail slot 58, respectively, formed in the flat abutting faces 52 and 54, respectively. The cooperating dove tail slot 58 and dove tail slide 56 guide the cooperating screw halves 48 and 50 for axial relative reciprocal movement as will be more particularly described hereinafter. The plane 23 intersects the rotational tool axis 36.

The alignment screw 46 includes a helical screw thread, generally designated 64, comprising a plurality of axially spaced apart, helically disposed half or partial screw threads 60 and 62, respectively, provided on the semi-cylindrical outer surfaces of the screw halves 48 and 50, respectively, which are of uniform pitch and radius. The partial screw threads 60 and 62 can be helically aligned with each other in any selected one of a plurality of axially spaced apart positions of the screw halves 48 and 50. In the positions of the screw halves 48 and 50 illustrated in FIGS. 5, 6, 8 and 9, the pluralities of partial screw threads 60 and 62 are coextensive and in helical alignment with each other. As illustrated, the axial length of the partial screw threads 60 is shorter than the axial length of the screw threads 62.

The tool 10 is particularly adapted for use in inserting a pair of fusion cages 66 and 68 (FIGS. 11 and 12) between vertically adjacent vertebrae 12 and 14 into drilled and tapped screw threads 71 and 73, respectively, provided on confronting portions 74 and 76, respectively, of the vertebrae 12 and 14, respectively. The fusion cages 66 and 68 may comprise titanium material and may be constructed as illustrated in the aforementioned U.S. Pat. Nos. 4,961,740; 5,015,247; 5,906,616; and 5,947,971. The fusion cages 66 and 68 include external helical threads 67 and 69 (FIG. 12) which are formed complemental to the tapped threads 71 and 73, respectively.

Figure 6:
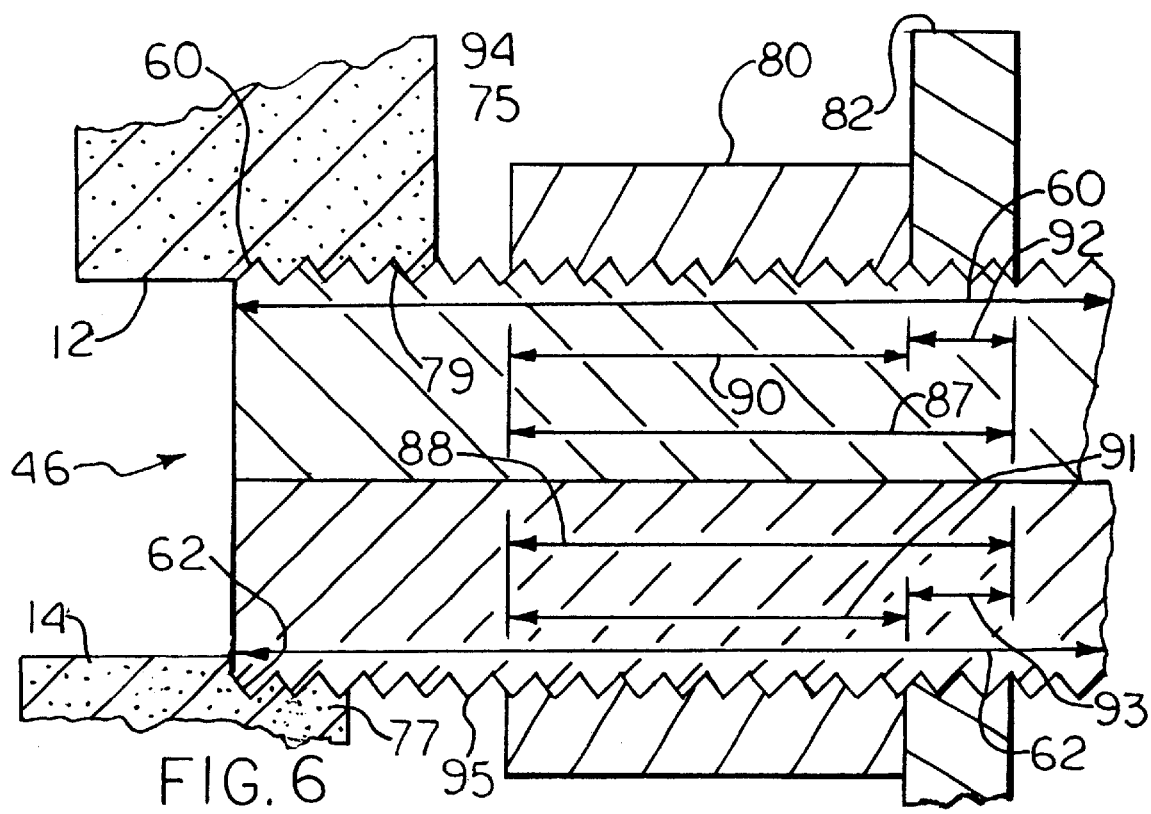
FIG. 6 is a greatly enlarged fragmentary side elevational view of the alignment tool more particularly illustrating a step in the process wherein the screw halves are initially threadedly coupled to a screw thread which has been tapped into confronting portions of the adjacent misaligned vertebrae.

The helical screw thread 64 is complementally formed to the screw threads 71 and 73 for threadedly receiving the alignment screw 46 when the screw halves 48 and 50 are in the positions illustrated in FIGS. 5, 6 and 8. The screw threads 71 and 73 are, of course, not continuous in the vertebrae but include first and second helically aligned, circumferentially and axially spaced flutes or leads 75 and 77 in vertebrae 12 and 14, respectively, separated by the intervertebral space between the vertebrae.

To ensure that the half screw threads 60 and 62 are maintained in helical alignment when the alignment tool 10 is turned about its axis 36 and threadedly coupled to and decoupled from the adjacent vertebrae 12 and 13, locking mechanism, generally designated 78, is provided and includes an alignment collar or nut, generally designated 80, and a locking collar or nut, generally designated 82. The alignment collar 80 and locking collar 82 are each internally threaded at 81 and 83, respectively, to threadedly receive the half screws 48 and 50 when the half screw thread 60 and 62 are in helical alignment or registry with each other.

The internal threads 81 and 83 on the alignment collar 80 and locking collar 82, respectively, are formed complementally to the screw thread 64 and will be unable to threadedly mate therewith unless the partial screw threads 60 and 62 are helically aligned. When the partial screw threads 60 and 62 are in helical registry, the alignment collar 80 and locking nut 82 can be freely threadedly received thereby to move from the inoperative dwell positions illustrated in FIGS. 9 and 10 to the locking positions illustrated in FIGS. 8 and 13. The locking nut 82 is threaded onto the aligned partial screw threads 60 and 62 into abutting engagement with the alignment collar 80 to preclude its axial movement relative to the half screws 48 and 50 and thus ensure that the screw threads 60 and 62 are maintained in helical alignment as the tool body 12 is rotated about its axis 36 and threadedly coupled to misalign vertebrae 12 and 14 or threadedly decoupled from the vertebrae 12 and 14 after the vertebrae 12 and 14 are repositioned to the aligned positions illustrated in claim lines in FIG. 5.

The half screws 48 and 50 have non-threaded dwell sections, generally designated 84 and 86, respectively, for threadedly receiving the alignment nut 80 and the locking nut 82 when the locking nut and alignment nut are unthreaded from the half screws 48 so as to allow the half screws 48 and 50 to be axially shifted relative to each other from the coextensive positions illustrated in FIG. 9 to the axially shifted positions illustrated in FIG. 10.

The Operation

With the vertebrae 12 and 14 are out of alignment, as illustrated in FIGS. 5 and 6, a hole 70 (FIGS. 11 and 12) is drilled on one lateral side of the spine 16 between the confronting portions 74 and 76 of the adjacent vertebrae 12 and 14 and tapped to provide a tapped helical screw thread 71 which is complementally formed to the screw thread 64. The formation of the helical screw thread 71 can be tapped with structure and in a manner more particularly described in U.S. Pat. No. 4,961,740 issued to Charles D. Ray on Oct. 9, 1990, which is included herein by reference as though fully recited herein, and/or the aforementioned German Patent publication No. 197503829 to provide adjacent helically disposed axially adjacent leads or flutes 75 and 77 in the confronting portions 74 and 76 of vertebrae 12 and 14, respectively (FIG. 6).

Initially, the screw halves 48 and 50 are disposed in the first axially coextensive positions illustrated in FIGS. 5, 6 and 8 with the first and second pluralities of half screw threads 60 and 62 being coextensive and in helical alignment with each other. In the positions of the parts as illustrated in FIGS. 5, 6 and 8, a first thread portion 87 of the first plurality of half screw threads 60 is aligned with a first thread portion 88 of the second plurality of half screw threads 62.

Initially, the alignment collar 80 is threadedly coupled to a first part 90 of the first thread portion 87 and a first part 91 of the first thread portion 88 of the second plurality of half screw threads 62. In the initial position of the parts illustrated in FIGS. 5, 6 and 8, the locking nut 82 is threadedly received by a second part 92 of the first thread portion 87 and a second part 93 of the first thread portion 88 of the second plurality of screw threads 62 to axially lock the alignment nut 80, lock nut 82 and screw halves 48 and 50 together and preclude relative axial shifting thereof.

With the parts in the locked positions illustrated in FIGS. 5, 6 and 8, the handle 21 is grasped and rotated to rotate the entire tool 10, including the body 12 and the screw 46, about the axis 36 in the direction of arrow 96 (FIG. 4) into the tapped screw thread 71 to a sufficient depth to anchor into the vertebrae and to a rotary position in which the axially inner end portion 94 of the axially adjacent leads or flutes 79 of half screw 48 is threadedly engages only the axially adjacent leads or flutes 75 of vertebrae 12 and the axially inner end 95 of axially adjacent leads or flutes 83 of half screw 50 threadedly engages only the axially adjacent leads or flutes 77 of second vertebrae 14. At this stage, the screw halves 48 and 50 will be in the positions illustrated in FIGS. 5, 6 and 8. The alignment nut 80 and locking nut 82 preclude any relative axial shifting of the half threads 60 and 62 while they are being threadedly inserted into the tapped thread 71 so that the tapped thread 71 is not damaged in any way that such relative shifting would otherwise cause.

The locking nut 82 is then unthreaded from the locking position illustrated in FIGS. 5 and 6 and 8 to an unthreaded dwell position, illustrated in FIG. 9, received by the non-threaded dwell section 84 and 86. Likewisely, the alignment collar or nut 80 is then turned about the axis 36 to an inoperative remote position received by the nonthreaded dwell sections 84 and 86. If desired, the locking nut and alignment nut 82 and 80, respectively, may be threaded on the axially inner threaded section 40 of the main body. (See FIG. 9).

Figure 7:
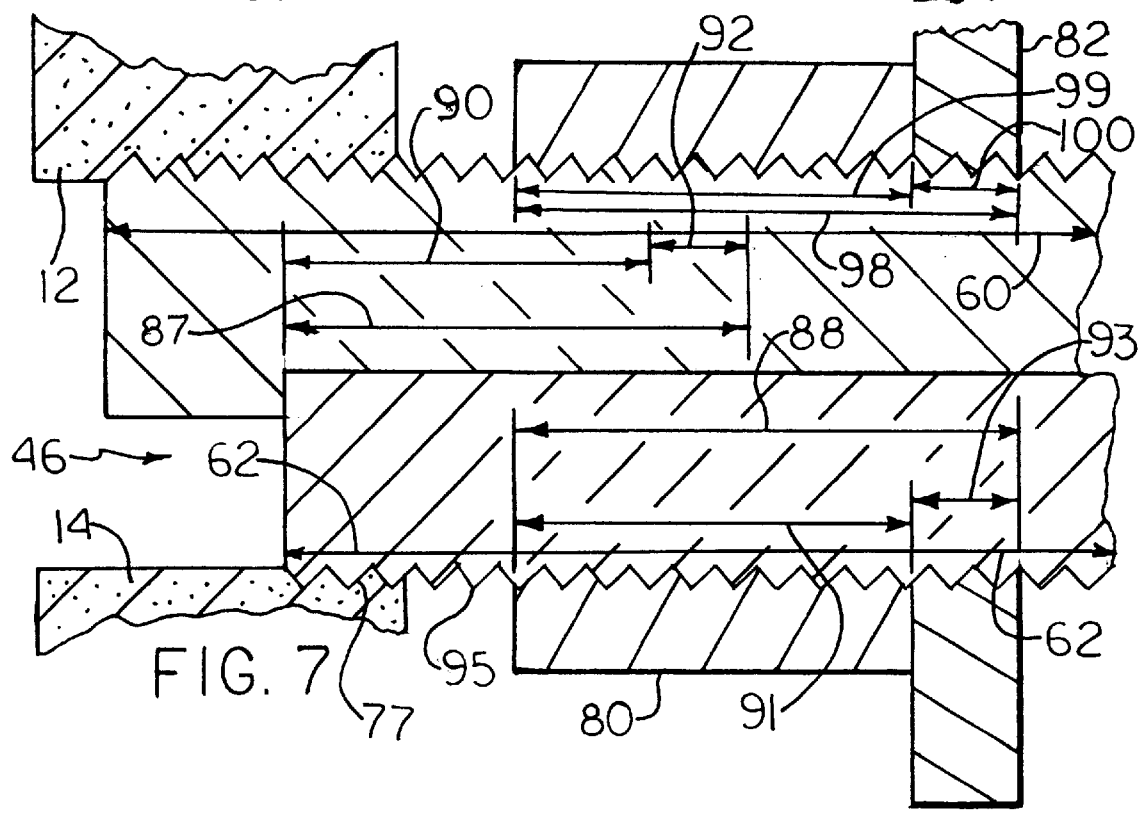
FIG. 7 is a similar enlarged fragmentary side elevational view illustrating a subsequent step in the method wherein the screw halves are relatively axially shifted to reposition the misaligned vertebrae into alignment.

With the parts thus positioned, the knob nut 32 is rotatably turned in a first direction, represented by the arrow 96, to axially inwardly move the rotary threaded tool body 26 relative to the main tool body 20 and thus axially translate the first half screw 48 axially inwardly in the direction of the arrow 89 relative to the second half screw 50 to the positions illustrated in FIGS. 7 and 10 to displace or reposition the vertebrae 12, in the direction of the arrow 89, into alignment with the second vertebrae 14. Pain, which is normally associated with misaligned vertebrae, in the positions illustrated in FIGS. 5 and 7, is frequently relieved when the vertebrae are repositioned as illustrated in FIG. 7.

It is important that, in the positions of the parts illustrated in FIGS. 7 and 10, the axially displaced partial screw threads 60 be helically aligned with the half screw threads 62 so that when the screw 46 is reversely by rotated in an opposite direction 97, opposite direction 96, the screw thread portions 60 and 62 follow in the same helical path as that defined by the tapped screw thread 71. If the partial screw threads 60 and 62 were to follow in different helical paths, they would damage the tapped thread 71 and thus preclude the subsequent insertion of the fusion cage 66.

Because the axially inner ends 94 and 95 of the half screws 48 and 50, respectively, are at this time threadedly disposed between the vertebrae 12 and 14, it is difficult for the surgeon to determine if the partial screw threads 60 and 62 are in or out of helical alignment with each other as they are being axially shifted from the position illustrated in FIG. 9 to the positions illustrated in FIGS. 7 and 10. Once the vertebrae 12 has been repositioned substantially in alignment with vertebrae 14 (FIG. 7), the operator will return the alignment nut 80 onto the screw 46.

If the partial threads 60 and 62 are not in helical alignment, the operator will be unable to thread the alignment collar 80 onto the first and second screw halves 48 and 50. Accordingly, the surgeon will attempt a trial and error procedure of axially relatively moving the screw halves 48 and 50 while concurrently attempting to rethread the alignment nut 82 onto the screw 46. When the partial screw threads 60 and 62 are in helical registry, alignment collar or nut 82 is freely threadedly received on the screw 46. The operator will continue to thread the nut 82 onto the screw halves 48 and 50 until it reaches the position illustrated in FIGS. 7 and 13.

Figure 13:
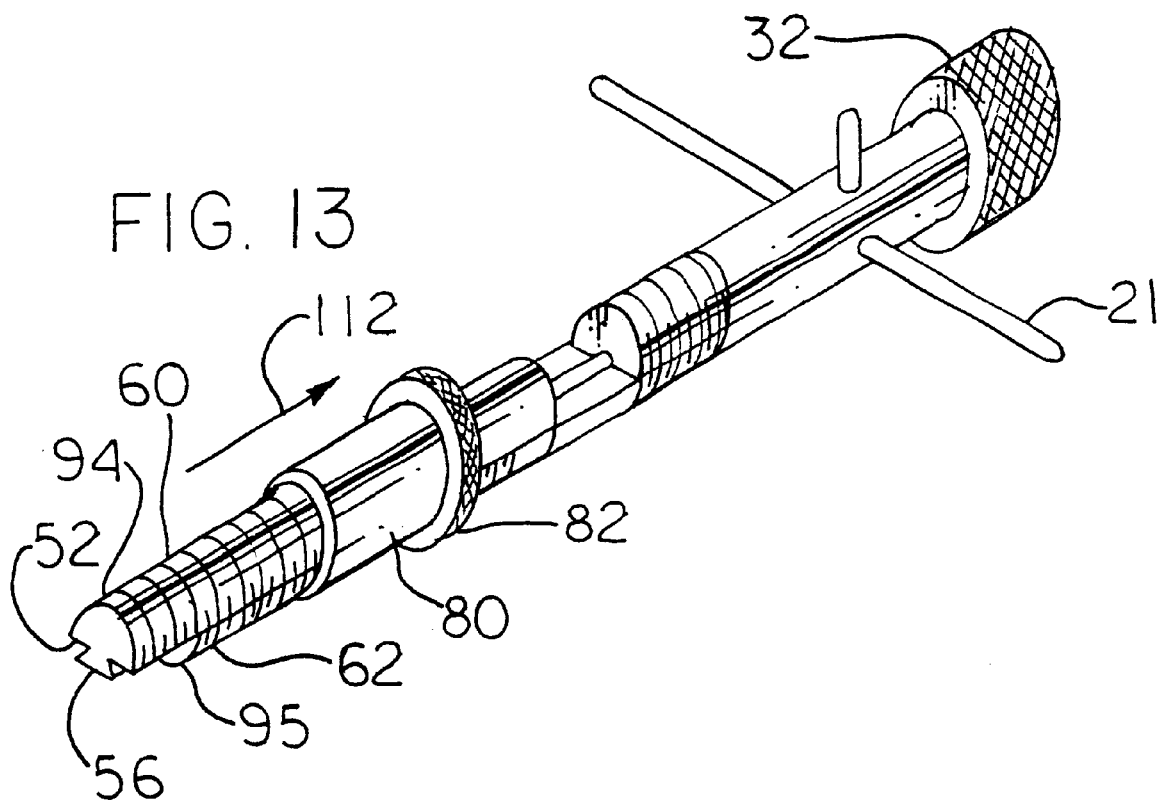
FIG. 13 is a similar perspective view illustrating the parts in the adjusted positions when the partible screw is being threadedly retracted from the now aligned vertebrae.

In the second axially adjusted positions of the parts illustrated in FIGS. 7 and 13, the first thread portion 88 of the second plurality of screw threads 62 is now aligned with a second portion 98 of the first plurality of partial screw thread 60. Moreover, the first part 91 of the second thread portion 88 is aligned with a first part 99 of the second thread portion 98 of the plurality of threads 60 and receives the alignment collar 82 thereon in said second positions of said first and second halves 48 and 50. Likewisely, the locking nut 82, which is again abutting the alignment nut 80, is received by the second thread part 93 of the second thread of the first thread portion 88 of the second plurality of screw threads 62 and a second thread part 100 of the second thread portion 98.

With the tool 10 holding the vertebrae 12 and 14 in alignment, a second hole 72 (FIGS. 11 and 12) is drilled and tapped with a thread 73 between confronting portion 74 and 76 of vertebrae 12 and 14 on the laterally opposite side of the axis 17 of the spinal column 16. A fusion cage 68, with threads complementally formed to the tapped screw thread 73, is threaded into the thread 73 in a manner more particularly described in U.S. Pat. No. 4,961,740 which is incorporated herein by reference.

Figure 11:
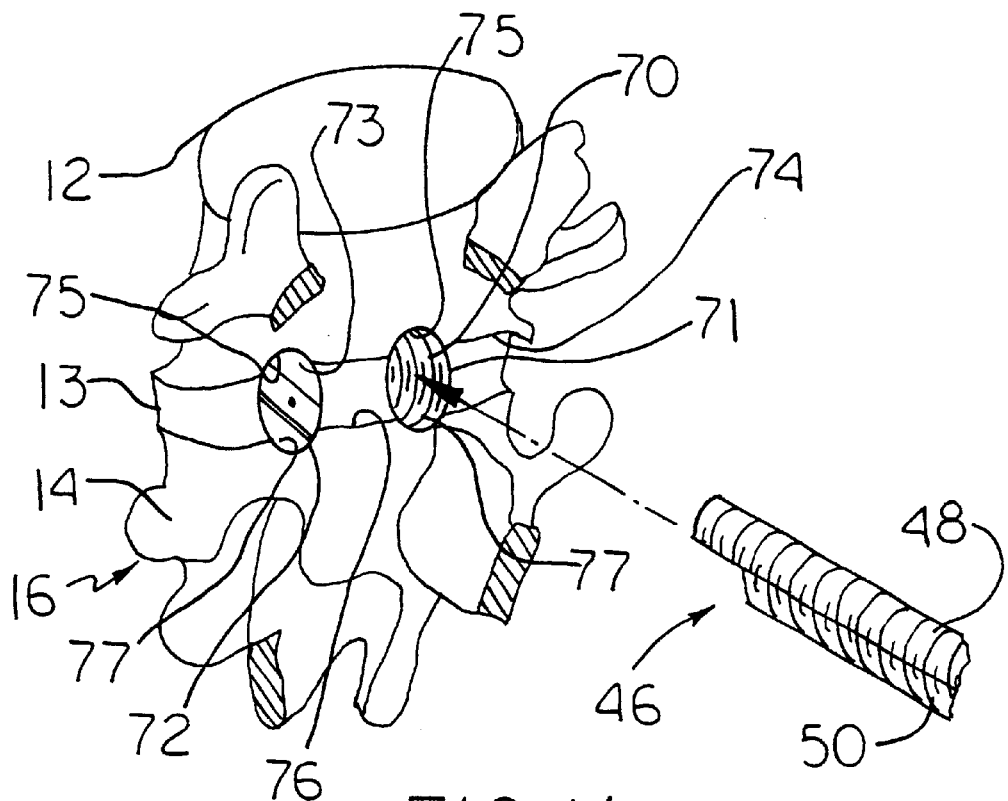
FIG. 11 is a similar perspective view illustrating a spinal column after the vertebrae have been aligned and the alignment tool in a subsequent step of the method wherein a second thread is tapped into opposing portions of the now aligned vertebrae, a fusion cage is threadedly received by the second thread, and the alignment tool has been unthreaded and axially removed from the now aligned vertebrae.
Figure 12:
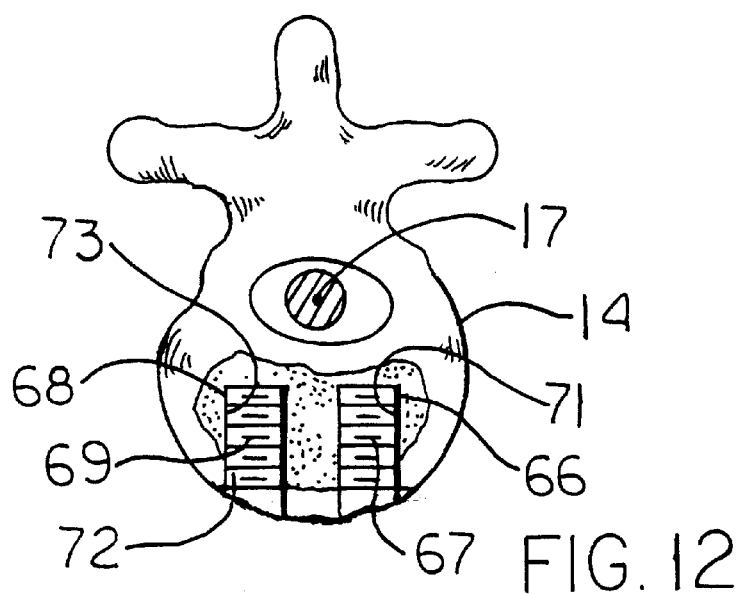
FIG. 12 is a top plan sectional view illustrating a pair of fusion cage screws threadedly positioned in the vertebrae to complete the process.

The fusion cage 68 will hold the vertebrae 14 and 16 in alignment and the tool 10 is reversely rotated in the direction of the arrow 97 about the tool axis 36 to threadedly remove the tool 10 from the first tapped thread 71 by turning the entire tool 10 about the axis 36 with the parts positioned as illustrated in FIGS. 11 and 13. The alignment collar 80 and locking collar 82 will hold the half screw threads 60 and 62 in helical alignment so that the screw thread 71 is not damaged by the removal. A second fusion cage 66 is then threaded into the first vertebrae tapped screw thread 71 to the position illustrated in FIG. 12.

The alignment collar 80 and locking nut 82 are again unthreaded from the screw 46 to be received in the dwell sections 84 and 86 in the positions illustrated in FIG. 10. The knob nut 32 is reversely turned in the direction of arrow 97 to axially retract the threaded body 26 and the screw half 48 in a direction 112 (FIG. 13) until the parts are returned to the positions illustrated in FIG. 9. The collars 80 and 82 are again threaded onto the alignment screw 46 to the positions illustrated in FIGS. 5, 6 and 8 and the operation can be repeated on as many adjacent vertebrae as need to be fused.

Alternate Embodiment

Figure 14:
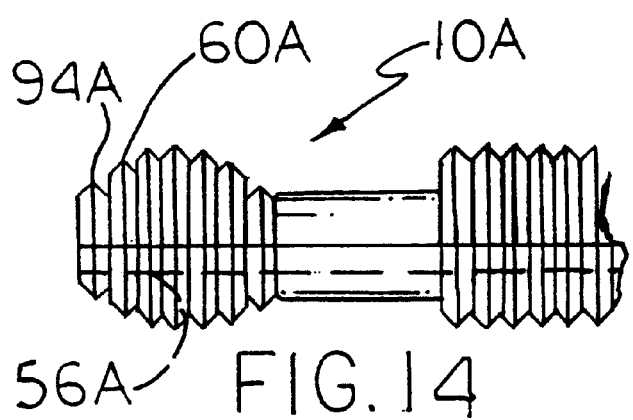
FIG. 14 is a fragmentary side elevational view of a slightly modified embodiment.

Referring now more particularly to FIG. 14, a slightly modified tool 10A is illustrated and generally similar parts are identified by generally similar reference characters followed by the letter A subscript. The alignment tool 10A is basically identical to the alignment tool 10 with the exception that the axial outer terminal end 94A of the first screw half 48A as illustrated as having a semi-spherically shaped tip which allows the tools 10A to be utilized when the adjacent vertebrae must be rotated about the axis 17 of the spinal column which allows the tool 10A to accommodate relative rotary movement of the vertebrae as they are being aligned. It should be understood that the second screw half may also have a tip with a similar complementally formed shape which cooperates with the tip 94A to define a barrel shaped tool.

Second Alternate Embodiment

A further slightly modified alignment tool, generally designated 10B, is illustrated in FIGS. 15–21 and generally similar parts will be identified by generally similar reference characters followed by the letter B subscript. The device 10B differs in that the elongate tool bodies 20B and 26B have abutting semi-cylindrical shapes which are substantially identically to the semi-cylindrical shapes of the half screws 50B and 48B, respectively. The dove tail slide 56B and the dove tail groove 58B extend the entire combined axial length of the alignment screw 46B and the tool body 20B.

Rather than relatively moving the elongate bodies 20B and 26B with the nut 32, a drive nut 32B is threadedly coupled, in the direction of arrow 96B, on the half threads 101 and 102 of elongate threaded bodies 20B and 26B which cooperate to provide a helical thread matching the internal thread 103 on the drive nut 32B. The drive nut 32B is axially restrained in opposite directions via axially spaced stops or holding collars 104 and 105 which are fixed to the elongate body 26B via threaded bolts 106 and 108, respectively, received in a pair of threaded receptacles 109 and 111, respectively, provided in elongate body 26B.

The screw half 50B includes a non-threaded dwell section 86B which receives the alignment nut 82B and locking nut 80B in a stowed position to allow the screw halves 48B and 50B to be axially displaced from positions illustrated in FIGS. 16, 18 and 19 to the positions illustrated in FIGS. 20 and 21. When the collars 80B and 82B are in the dwell positions illustrated in FIGS. 19 and 20, the tool 10B can be rotated in an opposite direction represented by the arrow 47B to turn the alignment screw 46B into the vertebrae tapped thread 71B.

Third Alternate Embodiment

Figure 22:
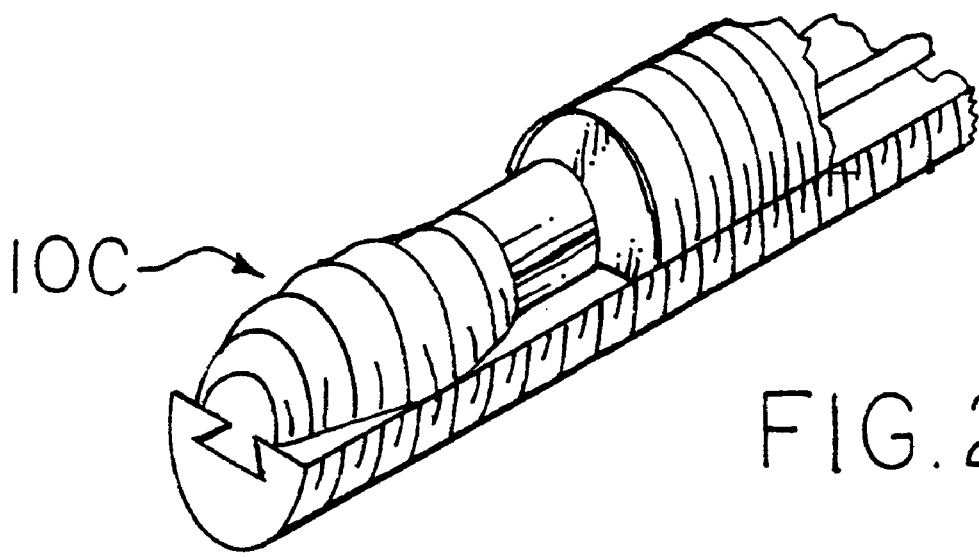
FIG. 22 is a slightly enlarged fragmentary view of yet another slightly modified embodiment.

A slightly modified alignment tool 10C is illustrated in FIG. 22 and is generally similar to the alignment tool illustrated in FIGS. 15–21 with the exception that the terminal end 94C includes a spherically shaped tip, similar to that illustrated in FIG. 14, which allows the tool to be utilized to align vertebrae that must be rotated about the vertical spinal axis 17 while the vertebrae being realigned.

It is to be understood that the drawings and descriptive matter are in all cases to be interpreted as merely illustrative of the principles of the invention, rather than as limiting the same in any way, since it is contemplated that various changes may be made in various elements to achieve like results without departing from the spirit of the invention or the scope of the appended claims.

What I claim is:

1. Apparatus for aligning first and second vertebrae which are misaligned and have confronting portions with at least one tapped thread adapted to receive a complementally threaded fusion cage, said apparatus comprising:

a partible screw, rotatable in first and second opposite directions about a longitudinal axis, for threadedly coupling to and decoupling from, respectively, said first and second vertebrae;

said partible screw including first and second relatively axially moveable screw halves having first and second pluralities of axially spaced, helically extending, partial screw thread sections, respectively which can be helically aligned with each other in any selected one of a plurality of different axially shifted locations to form a helical screw thread complementally formed to, and adapted to be received by, said tapped thread when said screw is turned in said first direction of rotation about said axis;

means for relatively axially shifting said first and second screw halves to first positions in which at least a first portion of said first plurality of partial screw thread sections is helically aligned with a first portion of said second plurality of partial screw thread sections when said screw is being rotated in said first direction about its axis and threadedly coupled to said first and second vertebrae, and for relatively axially shifting said first and second screw halves from said first positions to second positions, in which said first portion of said first plurality of partial screw thread sections is helically aligned with a second axially spaced portion of said second plurality of partial screw thread sections, to shift said first vertebrae into alignment with said second vertebrae; and locking means for detachably locking said first and second screw halves together in said second positions to preclude relative axial shifting of said first portion of said first plurality of screw threads section and said second portion of said second plurality of partial screw thread sections as said partible screw is rotated in said second direction and threadedly decoupled from said first and second vertebrae.

2. The apparatus set forth in claim 1 wherein said locking means comprises an alignment collar threadedly received by said first and second screw halves in said second positions.

3. The apparatus set forth in claim 2 wherein said locking means includes a locking collar threadedly received by said first and second screw halves in said second positions in abutting relation with said alignment collar to detachably lock said alignment collar to said first and second screw halves and preclude relative axial movement of said screw halves as said partible screw is being threadedly decoupled from said first and second vertebrae.

4. The apparatus set forth in claim 3 wherein said locking means includes means receiving first and second screw halves in said first positions for detachably locking said screw halves together in said first positions.

5. The apparatus set forth in claim 1 wherein said means for locking includes means for locking said first and second screw halves in said first positions to preclude relative axial shifting of said first and second screw halves as said partible screw is threadedly coupled to said first and second vertebrae.

6. The apparatus set forth in claim 5 wherein said locking means comprises an alignment collar axially shiftable relative to said first and second screw halves between a locking position threadedly received by said first and second screw halves in said first and second positions as said screw is being threadedly coupled to and decoupled from, respectively, said first and second vertebrae and axially spaced non-locking positions in which said screw halves can be axially relatively shifted.

7. The apparatus set forth in claim 5 wherein at least one of said first and second screw halves includes an axially spaced non-threaded dwell section for receiving said alignment collar in said non-locking position.

8. The apparatus set forth in claim 7 wherein said first and second screw halves include an additional axial spaced apart cooperating screw thread section on which said alignment collar can be threadedly coupled in said non-locking position.

9. The apparatus set forth in claim 6 in which said locking means includes a locking collar axially shiftable relative to said first and second screw halves between a locking position threadedly received by said first and second screw halves in either of said first and second positions and in abutting relation with said alignment collar as said partible screw is being threadedly coupled to and decoupled from, respectively, said first and second vertebrae, and an axially spaced, non-locking position in which said screw halves can be relatively axially shifted.

10. The apparatus set forth in claim 1 wherein said locking means includes an alignment collar threadedly receiving a first part of said first portion of said first plurality of partial screw thread sections and a first part of said first portion of said second plurality of partial screw thread sections when said first and second screw halves are in said first positions and threadedly receiving said first part of said first portion of said first plurality of partial screw thread sections and a first part of a second portion of said second plurality of partial screw thread sections when said first and second screw halves are in said second positions.

11. The apparatus set forth in claim 10 wherein said locking means includes a locking collar threadedly receiving a second part of said first portion of said first plurality of partial screw thread sections and a second part of said first portion of said second plurality of partial screw thread sections when said first and second screw halves are in said first positions; and threadedly receiving said second part of said first portion of said first plurality of partial screw thread sections and a second part of a second portion of said second plurality of partial screw thread sections when said first and second screw halves are in said second positions.

12. The apparatus set forth in claim 1 wherein said means for relatively axially shifting said first and second screw halves to said first and second positions comprises a hollow body having an elongate bore therethrough and an axial end mounted to an end of said first screw half; and an elongate threaded rod received by said elongate bore and having an axial end mounted to an end of said second screw half; and means threadedly coupled to said threaded rod for axially moving said threaded rod relative to said body.

13. The apparatus set forth in claim 1 wherein said means for relatively axially shifting said first and second screw halves, comprises first and second abutting elongate bodies each having opposite ends, mounted together for relative axial sliding movement;

means mounting said first and second halves on an end of said first screw and second abutting elongate bodies, respectively, for sliding movement therewith; and translating means coupled to opposite end portions of said first and second elongate bodies adjacent said opposite end portions of said elongate bodies.

14. The apparatus set forth in claim 13 wherein said translating means is threadedly coupled to at least one of said opposite end portions of said first and second elongate bodies.

15. The apparatus set forth in claim 14 wherein said elongate bodies each include a semi-cylindrical bar having a flat face slidingly coupled to the flat face of the other elongate body and a semi-cylindrical outer surface having a plurality of axially spaced, helically disposed rib sections which are in helical registry with the plurality of helically disposed rib sections on the other elongate body.

16. The apparatus set forth in claim 15 wherein one of said flat faces includes an elongate dove tail slot therein and the other of said flat faces includes complementally formed, dove tail slide slidingly received in said drive tail slot.

17. The apparatus set forth in claim 14 wherein at least one of said elongate bodies includes a curvilinear outer surface having a plurality of helically disposed rib sections forming a partial thread between the ends thereof; and translating nut means threadedly coupled to said partial thread for axially relatively shifting said elongate bodies.

18. The apparatus set forth in claim 13 wherein said locking means comprises an alignment collar which is received on said first and second elongate bodies in a non-locking position for axial movement thereon between said non-locking position and an axially outwardly spaced locking position receiving said screw halves.

19. The apparatus set forth in claim 18 wherein said locking means comprises an internally threaded collar that includes an axial outer portion which, in said locking position, threadedly receives an axially inner portion of said screw thread.

20. The apparatus set forth in claim 19 wherein said internally threaded collar includes an axially outer portion which, in said non-locking position, is threadedly coupled to a complementally threaded portion provided on at least one of said elongate bodies.

21. The apparatus set forth in claim 18 wherein at least said first elongate body includes a non-threaded dwell section axially spaced from said first plurality of screw thread sections for stowing said collar as said first and second screw halves are being relatively axially shifted between said first positions and said second positions.

22. The apparatus set forth in claim 21 further including a locking collar axially moveable on said first and second bodies between a second non-locking position received by said non-threaded dwell section and a second locking position received by said first and second pluralities of screw thread sections, in either of said first or second positions, in abutting engagement with said alignment collar.

23. The apparatus set forth in claim 1 wherein said screw has a barrel shape.

24. The apparatus set forth in claim 23 wherein each of said screw halves has a semi-cylindrical shape.

25. A vertebrae alignment tool for repositioning misaligned adjacent vertebrae into alignment comprising:
first and second elongate bodies, each having longitudinally spaced opposite ends, mounted together for relative longitudinal sliding movement;
a partible vertebrae shifting screw, having a longitudinal axis, for threadedly coupling to and decoupling from said adjacent vertebrae as said screw is turned in first and second opposite directions of rotation about said axis including;
first and second relatively longitudinally axially moveable screw halves having first and second pluralities of axially spaced, helically extending screw thread sections, respectively, which can be helically aligned with each other in any selected one of a plurality of different, longitudinally shifted positions to form a longitudinally extending helical screw thread;
said first screw half being mounted on one end of said first elongate body said second screw half being mounted on one end of said second elongate body;
shifting means threadedly coupled to at least one of said first and second elongate bodies
for longitudinally relatively moving said first and second elongate bodies to longitudinally relatively shift said first and second screw halves to first positions in which at least a first portion of said first plurality of screw thread sections is helically aligned with a first portion of said second plurality of screw thread sections as said screw is rotated in said first direction about said axis, and
for relatively longitudinally moving said first and second screw halves to second positions in which said first portion of said first plurality of screw thread sections is helically aligned with a second portion of said second plurality of screw thread sections; and
locking means detachably mounted on said screw halves to preclude axial shifting of said first portion of said first plurality of screw sections and said second portion of said second plurality of screw thread sections in said second positions when said screw is being oppositely rotated in said second direction to threadedly decouple from said vertebrae.

26. The vertebrae alignment tool set forth in claim 25 wherein said locking means is threadedly received by said first and second pluralities of screw thread sections.

27. The vertebrae alignment tool set forth in claim 26 wherein said locking means includes an alignment nut threadedly coupled to said screw when said first and second pluralities of screw thread sections are in said first positions to preclude relative longitudinal shifting thereof as said screw is rotated in said first direction and coupled to said vertebrae; said alignment nut being moveable to a decoupled position removed from threaded engagement with said first and second pluralities of screw thread sections to a non-coupling position as said screw thread sections are being longitudinally shifted.

28. The vertebrae alignment tool set forth in claim 26 including a locking nut threadedly coupled to said partible screw in abutting relation with said alignment nut when said first and second pluralities of screw thread sections are in said first positions and decoupled from said first and second pluralities of screw thread sections as said screw thread sections are being relatively longitudinally shifted.

29. The vertebrae alignment tool set forth in claim 28 wherein at least one of said ends of said first and second elongate bodies includes a dwell section on which said alignment nut and said locking nut rest when decoupled from said screw.

30. The apparatus set forth in claim 29 wherein said shifting means includes
a helical screw rib at least one of said elongate bodies; and
a translating nut rotatably mounted for rotation about said axis on the other of said elongate bodies and threadedly coupled to at least said one elongate body for relatively axially moving said elongate bodies to relatively axially move said screw halves; and
a hand graspable handle mounted on said other elongate body for preventing rotation of said other body as said translating nut is being rotated thereon.

31. A vertebrae alignment tool for shifting misaligned adjacent vertebrae into alignment with each other comprising:
first and second elongate bodies, each having longitudinally spaced opposite ends, mounted together for relative longitudinal sliding movement;
a vertebrae shifting partible screw, having a longitudinal axis, for threadedly coupling to and decoupling from said adjacent vertebrae as said screw is turned in first and second opposite directions, respectively, about said axis including
first and second longitudinally relatively axially moveable screw halves having first and second pluralities of axially spaced, helically extending screw thread sections, respectively, which can be helically aligned with each other in any selected one of a plurality of different, longitudinally shifted positions to form a longitudinally extending helical screw thread;
said first screw half being mounted on one end of said first elongate body;
said second screw half being mounted on one end of said second elongate body;
shifting means threadedly coupled to at least one of said first and second elongate bodies for longitudinally relatively moving said first and second elongate bodies to longitudinally relatively shift said first and second screw halves to first positions in which at least a first portion of said first plurality of screw thread sections is helically aligned with a first portion of said second plurality of screw thread sections as said screw is turned in said first direction of rotation about said axis, and for relatively longitudinally moving said first and second screw halves to second positions in which said first portion of said first plurality of screw thread sections is helically aligned with a second portion of said second plurality of screw thread sections; and alignment nut means detachably threadedly received by said screw when said first and second pluralities of thread sections are in either of said first positions or said second positions but moveable to an inoperative, position when said screw halves are being axially shifted.

32. The vertebrae alignment tool set forth in claim 31 including locking nut means threadedly received by said first and second pluralities of thread sections in either of said first positions or said second positions but moveable to an inoperative position removed from said first and second pluralities of thread sections as said screw halves are being axially shifted.

33. An alignment tool for shifting first and second misaligned adjacent vertebrae into alignment comprising:

a partible vertebrae shifting screw, having a longitudinal axis, for threadedly coupling to and decoupling from said adjacent vertebrae as said screw is rotated in first and second opposite directions about said axis;

said partible vertebrae shifting screw including
first and second relatively axially reciprocally moveable screw halves having first and second pluralities of axially spaced, helically extending, partial screw thread sections, respectively, which can be helically aligned with each other in any selected one of a plurality of different axially shifted locations to form a helical screw thread;

means for relatively axially shifting said first and second screw halves to first positions in which at least a first portion of said first plurality of partial screw thread sections is helically aligned with a first portion of said second plurality of partial screw thread sections to follow the same helical path when said screw is being rotated in said one direction and threadedly coupled to said first and second vertebrae, and for relatively axially shifting said first and second screw halves to second positions in which said first portion of said first plurality of partial screw thread sections is helically aligned with a second axially spaced portion of said second plurality of partial screw thread sections to shift said first vertebrae into alignment with said second vertebrae; and an alignment nut detachably threadedly received by said screw when said first and second pluralities of screw thread sections are in either of said first and second positions but detached from screw as screw first and second screw halves are being axially shifted.

34. The alignment tool set forth in claim 33 further including a locking nut detachably threadedly received by said first and second pluralities of screw thread sections in either of said first and second positions and abutting said alignment nut to lock said alignment nut in position to said first and second screw halves and preclude relative axial shifting of said first are second screw halves as said screw is being threadedly coupled to and decoupled from said adjacent vertebrae.

35. Apparatus for aligning first and second misaligned vertebrae which have confronting portions with at least one tapped thread adapted to threadedly receive a complementally threaded fusion cage, said apparatus comprising:

a vertebrae shifting partible screw, having a longitudinal axis for threadedly coupling to and decoupling from said first and second vertebrae when rotated in first and second opposite directions, respectively, about said axis including:
first and second relatively axially reciprocally moveable screw halves having first and second pluralities of axially spaced, helically extending, partial screw thread sections, respectively;
each of said first and second pluralities of axially spaced, helically extending partial screw thread sections including first and second axially spaced thread portions cooperating to form a helical screw thread;

means for relatively axially shifting said first and second screw halves to first positions in which
at least said first thread portion of said first plurality of partial screw thread sections is helically aligned with said first portion of said second plurality of partial screw thread sections to follow in the same helical path as said screw is rotated in said one direction, and
said first and second pluralities of partial screw thread sections in said first positions are each threadedly coupled to only one of said first and second vertebrae, and for relatively axially shifting said first and second screw halves to second positions in which said first portion of said first plurality of partial screw thread sections is in helical registry with said second axially spaced portion of said second plurality of partial screw thread sections to shift said first vertebrae into alignment with said second vertebrae; and alignment means detachably threadedly received by said first and second screw halves in said second positions to maintain said first plurality of partial screw sections and said second portion of said second plurality of partial screw thread sections in helical registry and insure that said first and second pluralities of thread sections follow in the same helical path as said screw is rotated in said second direction and unthreaded from said adjacent vertebrae.

36. The apparatus set forth in claim 35 including locking nut means detachably threadedly received by said first and second halves in abutting relation with said alignment means for detachably locking said alignment means to said first and second halves.

37. The apparatus set forth in claim 36 wherein said alignment means comprises an alignment collar which is detachably threadedly received by said first and second pluralities of partial screw thread sections when said screw halves are in either of said first positions or said second positions;
said alignment means comprises an alignment nut which is axially threadedly received in an alignment position by said first and second screw halves in either of said first or second positions but moveable to a non-aligning remote position removed from said screw halves;
said means for relatively axially shifting said first and second screw halves comprising first and second elongate bodies each having one end mounting said first and second screw halves, respectively, for movement therewith;

said one end including a nut receiving portion for receiving and stowing said nut in said non-aligning remote position.

38. Apparatus for aligning adjacent misaligned vertebrae comprising:

an elongate main tool body having a longitudinal bore therethrough and opposite ends;

an elongate rod, having opposite ends, slidably received in said bore;

a vertebrae repositioning screw, rotatable about a longitudinal axis in first and second opposite directions, having an external helical screw thread for threadedly coupling to and decoupling from said adjacent vertebrae as said screw is rotated in said first and second directions, respectively;

said screw comprising first and second complementally formed abutting screw halves having complementally formed half threads which can be helically aligned with each other in any selected one of a plurality of relatively axially spaced positions in which said half threads are helically aligned to form said screw thread;

one of said screw halves being mounted on an end of said elongate rod and the other of said screw halves being mounted to an end of said elongate tool body;

means for axially displacing said elongate rod relative to said main tool body to axially relatively move said screw halves between coextensive positions and axially displaced positions; and locking means detachably threadedly received by said first and second screw halves in either of said coextensive positions or said axially displaced position for selectively axially locking said screw halves together in either of said coextensive positions or said axially displaced positions to preclude relative axial movement of said screw halves as said screw is being threadedly coupled to and decoupled from said vertebrae and for unlocking said screw halves as said one screw half is being axially moved between said coextensive and said axially displaced position.

39. The apparatus set forth in claim 38 wherein said locking means comprises a sleeve mounted on said elongate rod and said main tool body for longitudinal movement between a locking position detachably threadedly coupled to said screw halves when said screw is being coupled to and decoupled from said vertebrae and a non-threaded, axially removed position when said rod and said main tool body are being axially displaced.

40. The apparatus set forth in claim 38 wherein said locking means comprises a hollow threaded locking collar mounted on said elongate rod and said tool body for movement between an axially displaced, non-locking position when said screw is being coupled to said vertebrae and a locking position detachably threadedly received by said screw halves and disposed in abutting relation with said sleeve.

41. A vertebrae aligning tool for aligning first and second adjacent misaligned vertebrae comprising:

an axially partible vertebrae shifting tool head, having an external helical screw thread thereon, mounted for rotation in first and second opposite directions about a longitudinal axis to threadedly couple to and decouple from, respectively, confronting portions of said adjacent misaligned vertebrae;

said partible tool head including first and second axially slidably coupled tool head sections having first and second complementally formed partial screw threads, respectively, of the same pitch, which can be disposed in helical registry with each other, in any selected one of a plurality of different, axially spaced positions to form said screw thread;

said first and second tool head sections in at least one rotary position being threadedly coupled to only one of said first and second misaligned vertebrae;

means for axially displacing said tool head sections relative to each other, when said first and second tool head sections are in said one rotary position and threadedly coupled to only one of said first and second misaligned vertebrae, between any selected one of said plurality of axially spaced positions to relatively shift said first and second adjacent misaligned vertebrae into substantial alignment with each other; and axial locking means detachably threadedly received by said first and second tool head sections for detachably axially locking said first and second screw halves together in said selected one of said axially spaced positions to selectively preclude relative axial movement of said first and second tool head sections when said tool is being threadedly coupled to and decoupled from said vertebrae but being threadedly moveable to a non-locking axially displaced position when said tool head sections are relatively axially moving between said plurality of axially spaced positions.

42. The vertebrae aligning tool set forth in claim 41 wherein said locking means comprises an internally threaded collar which can be concurrently detachably threaded onto said first and second screw partial screw threads of said first and second tool head sections when said first and second partial screw threads are in helical registry with each other to axially move thereon between said stowed non-locking position and a locking position threadedly received by said first and second partial threads.

43. The vertebrae aligning tool set forth in claim 41 wherein said locking means comprises an alignment nut which is threadedly received by said first and second partial screw threads when said first and second partial screw threads are helically aligned.

44. The vertebrae aligning tool set forth in claim 43 wherein said locking means includes a lock nut which is threadedly received by said first and second partial screw threads when said first and second partial screw threads are helically aligned for detachably axially locking said alignment nut to said first and second partial screw threads.

45. In an apparatus for repositioning adjacent misaligned vertebrae which have confronting portions with at least one tapped thread adapted to threadedly receive a complementally threaded fusion cage, said apparatus including a longitudinal, partible vertebrae shifting screw which can be rotated in one direction about an elongate axis to threadedly couple to said tapped thread of said adjacent misaligned vertebrae and in an opposite direction of rotation to threadedly decouple from said vertebrae;

said vertebrae shifting screw including first and second elongate screw thread sections which are longitudinally moveable relative to each other and include first and second pluralities of screw thread sections, respectively, which when said screw is in at least one rotary position, are each in threaded engagement with only one of said misaligned vertebrae when said screw is threadedly coupled to said vertebrae;

means for relatively longitudinally translating said first and second screw sections, when said screw is in said one rotary position, between first positions in which a first portion of said first plurality of screw thread sections is in registry with a first portion of said second plurality of screw thread sections and second positions in which said first portion of said first plurality of screw thread sections is in registry with a second portion of said second plurality of screw thread sections to relatively shift said misaligned vertebrae into alignment;

the improvement comprising:

alignment means for detachably threadedly engaging said screw thread sections in said second positions and maintaining said first and second pluralities of screw thread sections in registry as said screw is oppositely rotated in said opposite direction of rotation.

46. The apparatus set forth in claim 45 wherein said alignment means includes an alignment nut which is detachably threadedly coupled to said first portions of said first and second pluralities of screw thread sections when said first and second screw sections are in said first position and said screw is being rotated about said axis in said one direction and detachably coupled to said first and second portions of said first and second pluralities of screw thread sections, respectively, when said first and second screw sections are in said second positions and said screw is being decoupled from said vertebrae.

47. The apparatus set forth in claim 46 wherein said alignment means includes a locking nut which is threadedly coupled to said first and second pluralities of screw sections, in each of said first and second positions, in abutting relation with said alignment nut to detachably lock said alignment nut to said screw.

48. An alignment tool for repositioning misaligned adjacent vertebrae comprising:

an axially partible vertebrae displacing head rotatable in first and second directions about a longitudinal axis for threadedly coupling to and decoupling from, respectively, said adjacent vertebrae, said head including first and second axially slidably coupled head sections provided with first and second screw thread sections, respectively, which are helically aligned with each other in first axial positions to form a helical screw thread as said head is rotated in one direction about said axis;

means for relatively axially slidably shifting said first and second head sections from said first axial positions to second, axially displaced positions in which portions of said first and second screw thread sections are helically aligned and said misaligned vertebrae are moved into alignment with each other: and means threadedly receiving parts of said portions of said first and second screw thread sections when said first and second head sections are in said second, axially displaced positions for maintaining said first and second screw thread sections helically aligned as said head is oppositely rotated in said second direction to threadedly decouple from said vertebrae.

49. The tool set forth in claim 48 wherein said means threadedly receiving said parts of said portions of said first and second screw thread sections comprises an alignment collar threadedly received by said parts of said first and second portions when said first and second head sections are in either of said first or second positions, and but removed to a remote non-threaded position as said head sections are being relatively shifted.

50. The tool set forth in claim 49 wherein said means threadedly receiving said parts of said portions of said first and second screw thread sections comprises a locking collar disposed in abutting relation with said alignment collar and threadedly received on said parts of said first and second screw thread sections when said first and second head sections are in either of said first positions or said second positions but not when said first and second head sections are being axially shifted.

51. A method of aligning first and second vertebrae which are misaligned with an alignment tool comprising a partible screw having a longitudinal axis and including first and second screw halves provided with first and second pluralities of axially spaced helically extending partial screw thread sections, respectively, that can be helically aligned with each other in any selected one of a plurality of different axially shifted positions to form a helical screw thread on said screw, said method comprising:

axially relatively shifting said first and second screw halves to first positions in which at least a first portion of said first plurality of partial screw thread sections are helically aligned with a first portion of said second plurality of partial screw thread sections;

threadedly coupling said partible screw, with said first and second screw halves in said first positions, to said adjacent vertebrae such that said first screw half is threadedly coupled to only said first vertebrae and said second screw half is threadedly coupled to only said second vertebrae;

axially relatively shifting said screw halves relative to each other to second positions in which said first portion of said first plurality of partial screw thread sections is helically aligned with a second axially spaced portion of said second plurality of screw thread sections to move said first vertebrae into alignment with said second vertebrae;

axially locking said first and second screw halves together in said second positions to preclude relative axial shifting of said first portion of said first plurality of screw thread sections and said second axially spaced portion of said second plurality of screw thread sections; and unthreading said partible screw from said first and second vertebrae with said first and second screw halves locked together.

52. The method set forth in claim 51 wherein said axially locking step is accomplished by threading a first collar onto said first and second screw halves in said second positions.

53. The method set forth in claim 52 wherein said axially locking step is accomplished by threadedly coupling a locking collar on said first and second screw halves in said second positions into axial abutting engagement with said first collar to preclude relative axial shifting of said first collar and said first and second screw halves.

54. The method set forth in claim 53 further including the additional locking step of axially locking said first and second screw halves together prior to said step of threadedly coupling to preclude relative axial shifting of said first and second screw halves as said partible screw is being threadedly coupled to said first and second vertebrae.

55. The method set forth in claim 54 further including the step of axially unlocking said first and second screw halves prior to said step of axially relatively shifting said first and second screw halves to said second positions.

56. The method set forth in claim 54 wherein said additional locking step of axially locking is accomplished by sequentially threading said first collar and said locking collar onto said first and second screw halves into abutting engagement with each other.

57. The method set forth in claim 55 further wherein said step of unlocking said first and second screw halves prior to said step of axially shifting is accomplished by threadedly uncoupling said first collar and said locking collar from said first and second screw halves.

58. The method set forth in claim 51 further including the additional step of locking said first and second screw halves together in said first positions prior to said step of threadedly coupling.

59. The method set forth in claim 58 wherein said additional step of locking is accomplished by threadedly coupling a first collar onto said first and second screw halves in said first positions.

60. The method set forth in claim 59 wherein said additional locking step is accomplished by threadedly coupling a locking collar on said first and second screw halves in said first positions into abutting engagement with said first collar to preclude relative axial shifting of said first collar and said first and second screw halves when said screw thread is being threadedly coupled to said first and second teeth.

61. A method of aligning misaligned adjacent vertebrae comprising the steps of:

threadedly coupling an axially partible vertebrae displacing head, having first and second abutting screw halves provided with half screw threads which are helically aligned to form a helical screw thread, along an axis to said adjacent vertebrae;

axially relatively shifting said first and second abutting screw halves in opposite directions to axially displaced positions to relatively shift said misaligned vertebrae into alignment with each other; and axially detachably locking said abutting screw halves together in said axially displaced positions with said half threads in helical alignment to preclude relative axial movement therebetween and axially unthreading said head from said vertebrae with said abutting screw halves axially locked together.

62. The method set forth in claim 61 wherein said step of locking is accomplished by threading an alignment collar on said vertebrae displacing head when said first and second screw halves are in said axially displaced positions and threading a locking collar on said vertebrae displacing head into abutting engagement with said alignment collar.

63. The method set forth in claim 61 wherein said step of threading is accomplished by threading an alignment collar onto said vertebrae displacing head and threading a locking collar onto said vertebrae displacing head into abutting engagement with said alignment collar when said first and second screw halves are in said axially displaced positions to preclude relative axial shifting of said screw halves relative to each other and relative to said alignment collar.

64. A method of aligning misaligned adjacent vertebrae having spaced apart confronting portions comprising:

drilling and tapping a first part of said confronting portions of said adjacent vertebrae to provide a first threaded receptacle having a helical thread formed about an elongate axis;

threadedly coupling an axially partible tool screw, having first and second abutting screw halves coupled together in generally coextensive positions in which first and second half screw threads provided on said first and second screw halves are helically aligned to provide a helical screw thread, about said axis into said threaded receptacle such that said first and second screw halves are only threadedly coupled to one of said adjacent misaligned vertebrae;

axially relatively shifting said first and second screw halves to move said misaligned vertebrae into alignment and -over said screw halves to axially spaced positions in which portions of said first and second screw threads are in helical alignment with each other;

drilling and tapping a second part of said confronting portions of said adjacent vertebrae to provide a second threaded receptacle having a second helical thread formed about a second laterally spaced apart elongate axis;

threading a hollow cage about said second axis into said second receptacle;

holding portions of said first and second half screw threads in helical alignment with each other and unthreading said partible tool screw from said first receptacle; and threading a second fusion cage into said first receptacle.

65. A method of aligning misaligned adjacent vertebrae with an alignment tool comprising a partible screw having axially inner and outer ends; and a longitudinal axis and including first and second screw halves having first and second longitudinally slidably coupled screw halves provided with first and second pluralities of partial screw thread sections which can be aligned with each other in a plurality of different axially spaced positions to form a helical thread on said screw, said method comprising:

axially relatively shifting said first and second screw halves to first positions in which at least a first portion of said first plurality of partial screw thread sections are helically aligned with a first portion of said second plurality of partial screw thread sections;

threading said partible screw between said adjacent misaligned vertebrae to a position in which said axially outer ends of each of said first and second pluralities of partial screw thread sections is disposed between said vertebrae but threadedly coupled to only one of said vertebrae, and axially inner ends of said thread and first and second pluralities of thread sections are exposed;

axially relatively shifting said screw halves relative to each other to second positions in which said first portion of said first plurality of partial screw thread sections is helically aligned with a second axially spaced portion of said second plurality of screw thread sections to move said first vertebrae into alignment with said second vertebrae; and threading at least one nut on said axially inner exposed ends of the first and second pluralities of partial screw thread sections when said screw halves are in said second positions to insure that said first and second pluralities of thread sections will follow in the same helical path as said screw is unthreaded from said adjacent vertebrae.

66. A method of aligning misaligned adjacent vertebrae comprising the steps of:

threadedly coupling one-half of a threaded alignment head, having a helical screw thread thereon, with one vertebrae and threadedly coupling another half of said threaded alignment head by rotating said alignment head about an axis between said adjacent vertebrae;

axially shifting said one-half relative to said another half to move said one vertebrae into alignment with said adjacent vertebrae; locking said one-half and said another half together with at least a portion of the helical screw thread on said one-half in helical alignment with a portion of the helical screw thread on said another half to preclude relative axial shifting of said one-half and said another half from said vertebrae and said another vertebrae while said one-half and said another half are locked together.

67. Apparatus for repositioning misaligned vertebrae comprising:

a vertebrae alignment head having first and second half portions forming first and second screw thread sections which cooperate to form a helical screw on said head;

said head being rotatable about a longitudinal axis in a first direction between said vertebrae to a position in which said first and second screw thread sections each threadedly engage only one of said vertebrae;

said head being oppositely rotatable about said axis in an opposite direction to an unthreaded position removed from said vertebrae;

means for axially relatively shifting said first and second halves in opposite directions to relatively move said vertebrae into alignment with each other; and means for axially detachably holding said first and second halves together with at least a portion of said first screw thread section in helical alignment with a portion of said second screw thread section to preclude relative axial shifting of said first and second screw thread sections when said head is rotated in said opposite direction.

68. Apparatus for relocating misaligned vertebrae which have confronting portions with at least one tapped thread, adapted to threadedly receive a complementally threaded fusion cage, said apparatus comprising:

a partible alignment screw having a rotational axis and first and second partial screw thread sections provided with first and second pluralities of partial screw threads, respectively, cooperating to define a helical screw thread complementally formed to and adapted to be threadedly received by, said tapped thread when said screw is rotated in one direction of rotation about said axis and decoupled from said tapped thread when said screw is oppositely rotated in a second direction;

said first and second partial screw thread sections being adapted to be threadedly coupled to only one of said vertebrae when said screw is received by said tapped thread;

said first and second partial screw thread sections being relatively axially reciprocally moveable between first position in which a first position of said first screw thread section is in helical alignment with a first portion of said second screw thread section and second axially displaced positions in which first portion of said first screw thread section is in helical alignment with a second portion of said second screw thread section to relatively shift and reposition said vertebrae; and locking means threadedly receiving said first and second partial screw threads when said first and second screw thread sections are in said second positions for locking said first and second screw thread sections in said second positions as said screw is being oppositely rotated in said second direction to prevent axial shifting of said first and second screw threads and damage to said tapped thread.

69. The apparatus set forth in claim 68 wherein said locking means comprises an alignment nut and a locking nut threadedly receiving said first and second partial screw thread sections and disposed in abutting engagement with each other.

70. A method of repositioning misaligned and spaced apart adjacent first and second vertebrae comprising the steps of tapping a first thread into confronting portions of said misaligned vertebrae;

turning a partible screw having first and second circumferentially spaced apart screw thread portions defining a screw thread complementally formed to said first thread, about its longitudinal axis in a first direction into said thread to threadedly couple said circumferentially spaced first and second screw thread sections of said screw to only said first and second vertebrae, respectively;

axially shifting said circumferentially spaced first and second thread sections relative to each other to axially displaced positions to relatively move said first and second vertebrae into substantial alignment;

threading at least one collar onto said circumferentially spaced first and second thread sections to maintain the relative positions of said first and second thread sections in said axially displaced positions; and unturning said partible screw in an opposite direction of rotation from said thread while said one collar is received by circumferentially spaced first and second thread sections.

71. The method set forth in claim 70 wherein said step of axially shifting includes the step of helically aligning said first and second screw threads sections in said axially displaced positions prior to said threading step and further including the step of threading a second locking collar onto said first and second screw thread sections in said axially displaced positions into abutting engagement with said one collar to said first and second screw thread sections.

72. The method set forth in claim 70 including the step of threading said one collar onto said first and second screw thread sections prior to said turning, step to detachably restrict relative axial movement of said first and second screw thread sections during said turning step; and unthreading said one collar from said first and second screw thread sections prior to said axially shifting step.

73. The method set forth in claim 71 further including the step of threading said second collar onto said first and second screw thread sections into abutting engagement with said one collar to lock said one collar to said first and second screw thread sections, and unthreading said second collar from said first and second screw thread sections prior to said step of axially shifting.

* * * * *